United States Patent
Gregory et al.

(10) Patent No.: US 10,070,897 B1
(45) Date of Patent: Sep. 11, 2018

(54) TRANSLATIONAL POSTERIOR CERVICAL POLYAXIAL SCREW

(71) Applicant: SPINE WAVE, INC., Shelton, CT (US)

(72) Inventors: Zachary Gregory, Shelton, CT (US); Fabio Pinto, Stamford, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 15/846,959

(22) Filed: Dec. 19, 2017

Related U.S. Application Data (60) Provisional application No. 62/570,248, filed on Oct. 10, 2017.

(51) Int. Cl.
*A61B 17/70* (2006.01)
*A61B 17/00* (2006.01)

(52) U.S. Cl.
CPC ...... *A61B 17/7037* (2013.01); *A61B 17/7032* (2013.01); *A61B 2017/00862* (2013.01); *A61B 2017/00982* (2013.01)

(58) Field of Classification Search
CPC ........ A61B 17/7032–17/7056; A61B 17/7001; A61B 17/7002; A61B 17/84; A61B 17/8605
USPC .................................. 606/246–279, 300–328
See application file for complete search history.

(56) References Cited

U.S. PATENT DOCUMENTS

| | | | |
|---|---|---|---|
| 8,044,272 B2 * | 10/2011 | Burdett | A23D 9/00 435/410 |
| 9,113,960 B2 * | 8/2015 | Hansell | A61B 17/7035 |
| 9,498,255 B2 * | 11/2016 | Lovell | A61B 17/7037 |
| 2015/0100096 A1 * | 4/2015 | Protopsaltis | A61B 17/7035 606/306 |

\* cited by examiner

*Primary Examiner* — Pedro Philogene
(74) *Attorney, Agent, or Firm* — Hoffmann & Baron, LLP (57) ABSTRACT

A translating polyaxial bone screw assembly for anchoring a connecting rod to a spinal vertebra comprises a bone screw having a threaded shank and a head coupled to a yoke. The yoke has at one end a rod receiving channel for receiving a connecting rod and an opposite end that is coupled to the bone screw by a coupling assembly. The coupling assembly couples the yoke for polyaxial movement relative to the bone screw and for translational movement of the yoke in a direction transverse to the axis of the bone screw. The coupling assembly comprises a biasing element supported for joint movement with the yoke that provides a manually surmountable tension force between the yoke and bone screw head that is maintained during polyaxial and translational movement. A fastening element is supported by the yoke for securing the connecting rod between the fastening element and the coupling assembly.

26 Claims, 10 Drawing Sheets

TRANSLATIONAL POSTERIOR CERVICAL POLYAXIAL SCREW

CROSS-REFERENCE TO RELATED APPLICATION

This application claims the benefit of U.S. Provisional Patent Application No. 62/570,248, filed Oct. 10, 2017, the entire contents of which are incorporated by reference herein.

FIELD OF THE INVENTION

The subject invention relates generally to the field of spinal fixation systems and more particularly to a bone screw assembly that incorporates translational and polyaxial fixation to the posterior cervical spine.

BACKGROUND OF THE INVENTION

Several techniques and systems have been developed for correcting and stabilizing injuries to, or malformation of, the spine. In one type of system, an elongated member such as an elongate bendable rod is disposed longitudinally along a length of the spine, spanning two or more vertebral levels. In certain applications, the rod is bent to correspond to the normal curvature of the spine in the particular region being instrumented, such as the normal kyphotic curvature of the thoracic region or the lordotic curvature of the lumbar region. In accordance with such a system, the rod is engaged to various vertebrae along a length of the spinal column by way of a number of anchor devices that utilize a variety of fixation elements configured to engage specific portions of the vertebra and other bones. For instance, one such fixation element is a hook that is configured to engage the laminae of the vertebra. Another very prevalent fixation element is a bone screw that can be threaded into various parts of the vertebrae, particularly the pedicle or lateral mass.

As these systems have evolved, various degrees of freedom of relative orientation were integrated into the systems in order to accommodate misaligned spinal curvature as well as to minimize rod bending and stress risers in the anchor. Presently, the standard in rod-based spinal systems is a polyaxial pedicle screw which includes a yoke having a slot for receiving a bendable elongate connecting rod that is coupled to a threaded bone engaging shank for polyaxial swiveling movement with respect thereto. One example of such a polyaxial screw is shown and described in commonly assigned U.S. Pat. No. 8,162,990, entitled "Multi-axial Spinal Fixation System", issued on Apr. 24, 2012 to Robert Potash et al. Further advances in the art have now seen anchor systems that include movement of the polyaxial rod-receiving yoke in an additional plane of motion relative to the bone fastener. Such an improved rod fixation element with additional degrees of freedom known as a translational screw is shown and described in commonly assigned U.S. Patent Publication No. 2015/0100096, entitled "Translating Polyaxial Screw", filed by Dimitri Protopsaltis et al. on Sep. 25, 2014, and incorporated herein by reference in its entirety. Another example of a translational screw is shown and described, in U.S. Pat. No. 9,763,701, entitled "Multiplanar Bone Anchor System", issued on Sep. 19, 2017 to Christopher Shaffrey et al.

While such translational screws provide beneficial aspects to surgeons, improvements are still desirable. For example, after screw placement in an operation there are often times when subsequent multiple steps need to be taken before a connecting rod for fixation can be placed and locked. During this time, it is desirable that the screw heads remain substantially stationary. Screw heads are often manipulated with a screw head positioner for later rod placement and for a preview of any rod contouring that must be done. Once the screw heads are positioned it is preferable that they stay in position, which negates the need for repositioning and therefore streamlines the operation. As such, if the heads are already aligned it makes it easier for the surgeon to determine the necessary contouring of connecting rods that need to be seated in the screw heads, thereby further simplifying the task.

SUMMARY OF THE INVENTION

It is an object of the invention to provide an improved translating polyaxial bone screw assembly for anchoring an elongate connecting rod to a vertebra of a spine. A further object is to provide a translating polyaxial bone screw assembly that includes a biasing element that applies a tension force between the rod-receiving yoke and the polyaxially supported bone screw sufficient to hold the yoke and the bone screw in a provisional position that is surmountable upon application of a manual force.

DESCRIPTION OF THE FIGURES

FIG. 3B is a cross-sectional view of the yoke as seen along viewing lines III B-III B of FIG. 3A.

FIGS. 8A and 8B are mutually orthogonal cross-sectional views of the assembled bone screw assembly of FIG. 1 prior to placement of the connecting rod and set screw.

DESCRIPTION OF THE EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
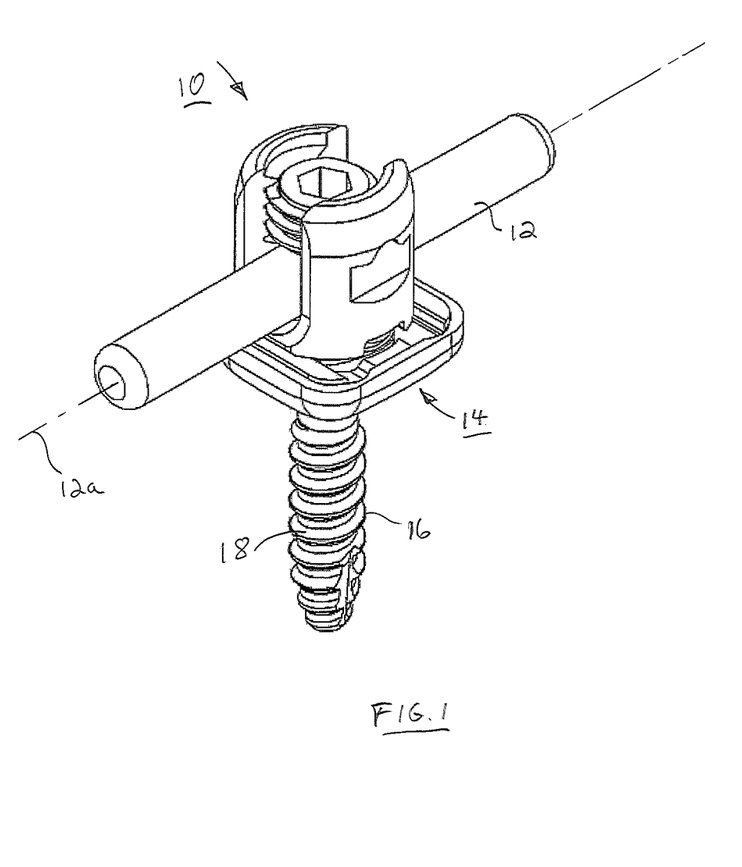
FIG. 1 is a top perspective view of a spinal fixation system utilizing a translating polyaxial bone screw assembly in accordance with an embodiment of the present invention shown in connection with an elongate connecting rod.

The present invention contemplates a spinal fixation system, such as the system 10 depicted in FIG. 1. As is known in the art, the spinal fixation system 10 spans between successive vertebrae of the spine. An elongated member, such as a connecting rod 12 defining an axis 12a, extends along the length of the spine and provides an anchor point for connecting each vertebra to the rod 12. The rod 12, typically formed of titanium or a titanium alloy, is contoured by bending to approximate the normal curvature of the spine for the particular instrumented spinal segments. A translating polyaxial bone screw assembly 14 is provided for connecting each of the vertebral segments to the rod 12. For the purposes of the present arrangement, polyaxial bone screw assembly 14 includes a bone engaging fastener 16 which is a bone screw, preferably a pedicle screw. The bone screw 16 includes a threaded elongate shank 18 configured for threaded engagement within a portion of a vertebra, such as the pedicle. More specifically, the polyaxial bone screw assembly 14 includes features, as will be described that provide for translating and polyaxial connection of the bone screw 16 to rod 12. In a particular example, the shank 18 is configured for engagement within the pedicle of a vertebra of the cervico-thoracic spine. Configurations for use in the lumbar spine and other regions of the spine are also contemplated. Further, while in this particular arrangement the bone engaging fastener is a bone screw, it should be appreciated that the bone engaging fastener may be a bone anchor device that may include hooks, bolts, or other means for engaging a vertebra.

Figure 2:
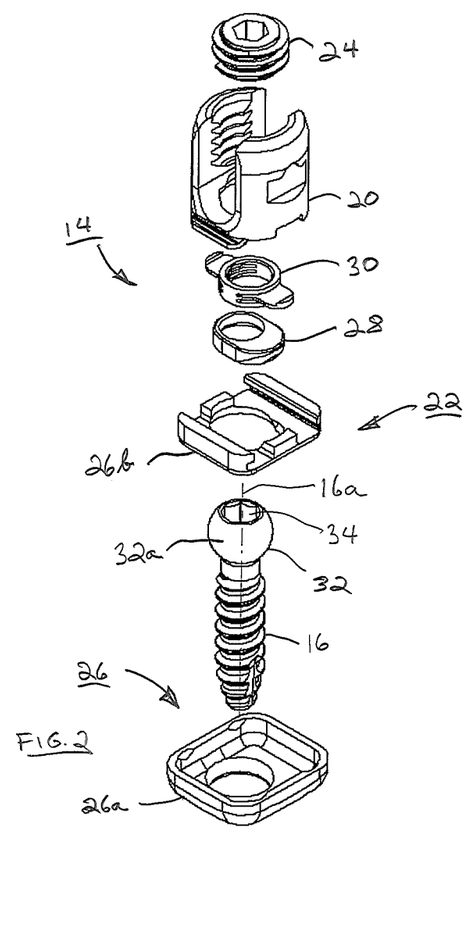
FIG. 2 is a top perspective exploded view of the translating polyaxial bone screw assembly of FIG. 1.
Figure 2B:
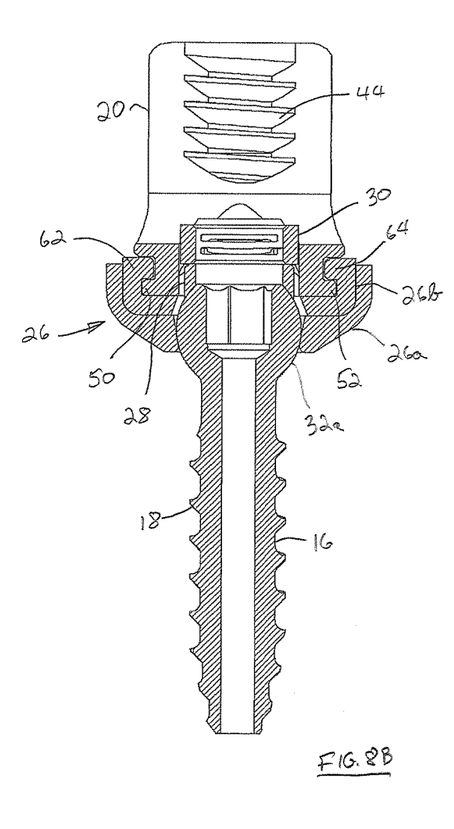

Referring now also to FIG. 2, the elements of translating polyaxial bone screw assembly 14 are shown in exploded view. Bone screw assembly 14 comprises bone screw 16, a yoke 20, a coupling assembly 22 coupling yoke 20 to bone screw 16, and a fastening element 24. Coupling assembly 22 comprises a base 26, a pressure element 28 and a spring element 30. Base 26 includes a lower base 26a and an upper base 26b. These components of bone screw assembly are described in detail, as follows.

Still referring to FIG. 2, bone screw 16 includes a head 32 by which bone screw 16, and ultimately the vertebra, are anchored to the spinal rod 12. In accordance with one arrangement, head 32 defines an internal socket 34 which may have a hexagonal shape or other configuration suitable for engagement with an instrument for threadably attaching bone screw 16 to a vertebra. Threaded elongate shank 18 defines a bone screw axis 16a extending longitudinally through shank 18 and socket 34. Outer surface 32a of head 30 in the described arrangement is substantially spherical.

Figure 3A:
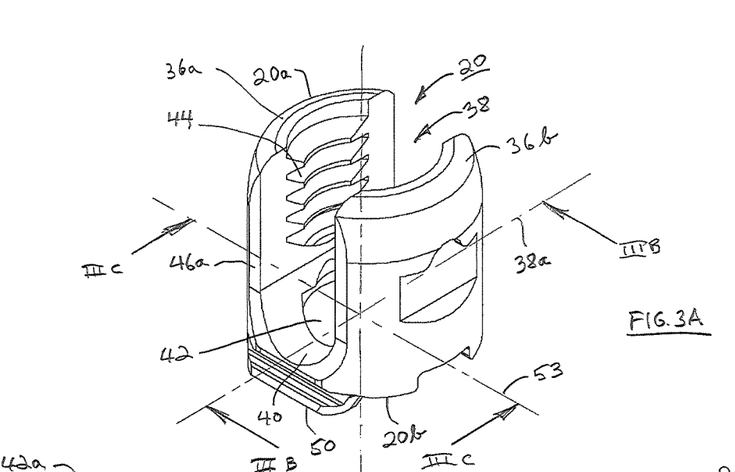
FIG. 3A is a top perspective view of the yoke of the bone screw assembly of FIG. 1.
Figure 3B:
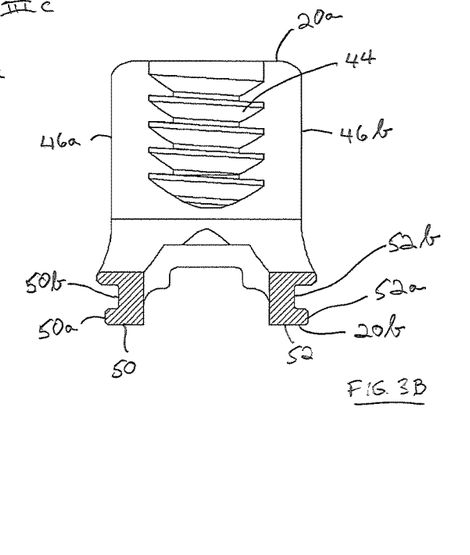
FIGS. 3B and 3C are cross-sectional views of the yoke as seen along viewing lines III B-III B and III C-III C, respectively of FIG. 3A.
Figure 3C:
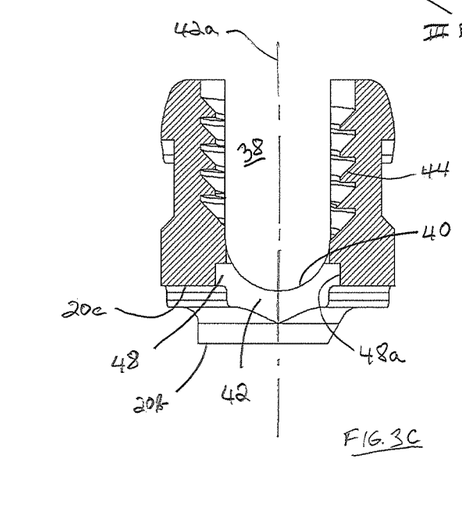
Figure 10A:
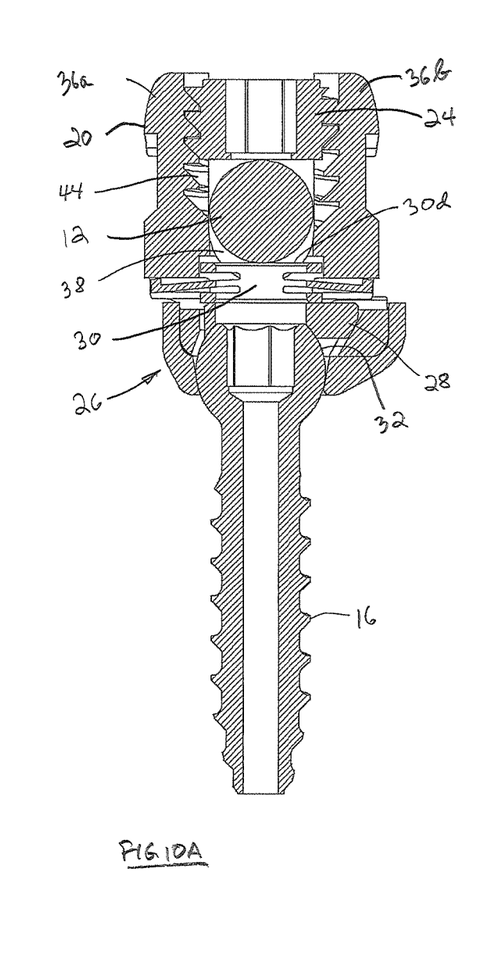
FIG. 10A is cross-sectional views of the assembled bone screw assembly of FIG. 1 after placement of the connecting rod and set screw with the yoke aligned with the axis of the bone screw.
Figure 10B:
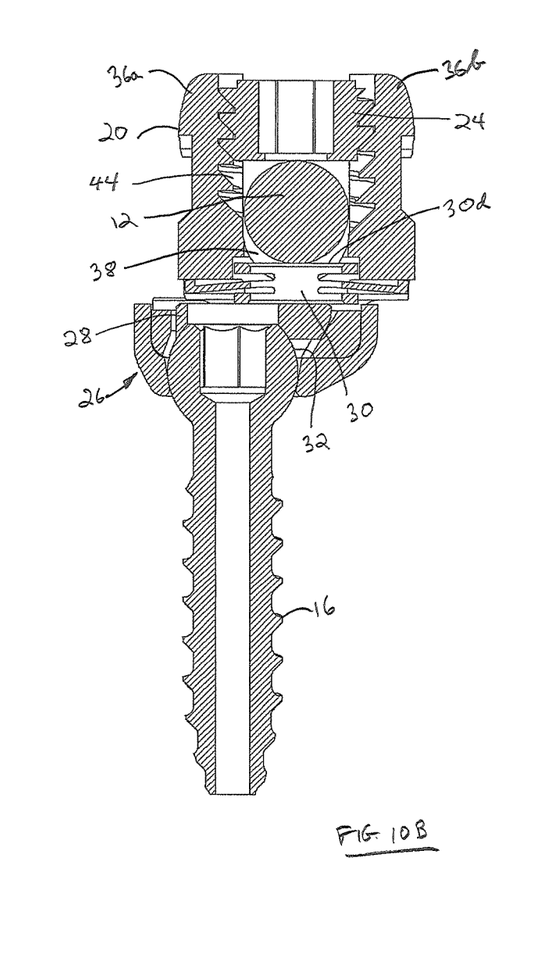
FIG. 10B is the cross-sectional views of the assembled bone screw assembly of FIG. 10A showing the yoke in a translated position relative to the bone screw.

Turning now to FIGS. 3A, 3B and 3C, details of yoke 20 are described. Yoke 20 is of generally cylindrical configuration having an upper end 20a and an opposite lower end 20b. Yoke 20 includes a pair of spaced opposing arms 36a and 36b that define therebetween a yoke channel 38 having a channel axis 38a that extends through upper yoke end 20a. The gap between arms 36a and 36b, and consequently the width of the channel 38, is sized to closely fit spinal rod 12, as best seen in FIGS. 10A and 10B. Yoke 20 includes a surface 40 at the bottom of channel 38, surface 40 extending between and joining yoke arms 36a and 36b. The bottom surface 40 in one arrangement is formed as a curved surface and has an opening 42 extending therethrough in communication with channel 38 and defining a yoke opening axis. 42a. Arms 36a and 36b define internal threads 44 for engaging fastening element 24, as will be further described. Yoke 20 is truncated on either side of channel 38 by a pair of spaced opposing flat surfaces 46a and 46b that define external surfaces of arms 36a and 36b. Flat surfaces 46a and 46b are substantially parallel to each other and are disposed generally perpendicular to channel 38 that extends through flat surfaces 46a and 46b and that is configured to receive spinal rod 12. Yoke opening 42 includes a counterbore 48 extending into yoke 20 at the opposite end 20b thereof, counterbore 48 being defined by a generally cylindrical inner surface 48a having a diameter greater than the width of channel 38, as illustrated in FIG. 3.

Opposite end 20b of yoke 20 is formed to include a pair of spaced substantially parallel rails 50 and 52 extending across opposite end 20b of yoke 20 along a translation axis 53 transverse to channel axis 38a for cooperative sliding coupling with base 26, as will be described. In a particular arrangement, translation axis 53 and channel axis are substantially orthogonal. Each rail 50 and 52 is disposed on opposite sides of the yoke opening 42. In one aspect, each rail 50 and 52 includes an outwardly projecting flange 50a and 52a, respectively, and an inwardly directed groove 50b and 52b, respectively, as shown in FIG. 3B. As such, rails 50 and 52 together form a T-bar configuration for slidable cooperative fit with a T-bar slot of base 26, as will be described. Extending interiorly of rails 50 and 52 adjacent counterbore 48 and transversely relative to yoke axis 42a is contact surface 20c for engagement with spring element 30, as will be described.

Figure 4A:
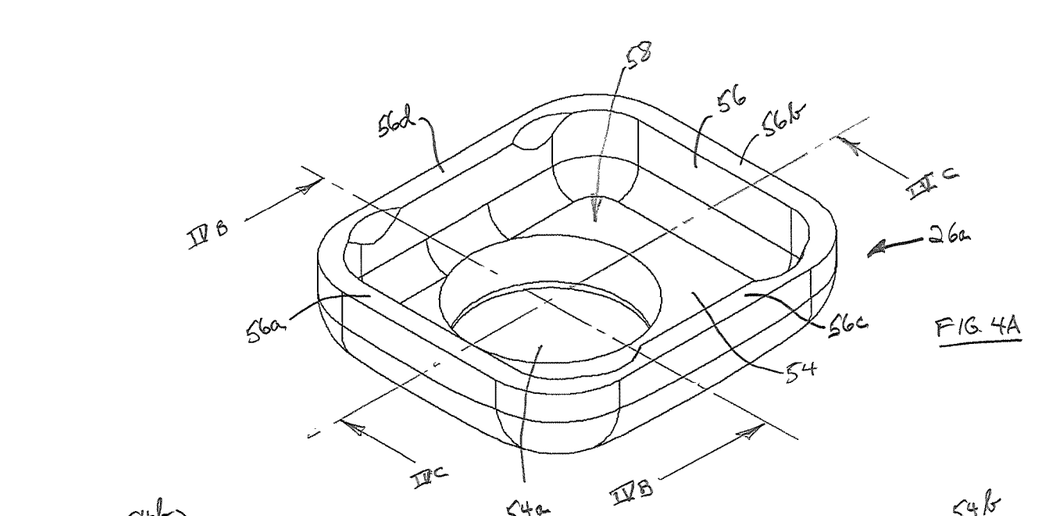
FIG. 4A is a top perspective view of the lower base of the bone screw assembly of FIG. 1.
Figure 4B:
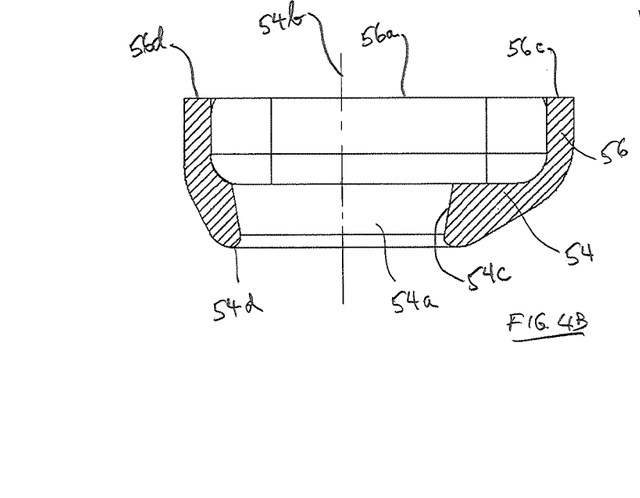
FIGS. 4B and 4C are cross-sectional views of the lower base as seen along viewing lines IV B-IV B and IV C-IV C, respectively of FIG. 4A.
Figure 4C:
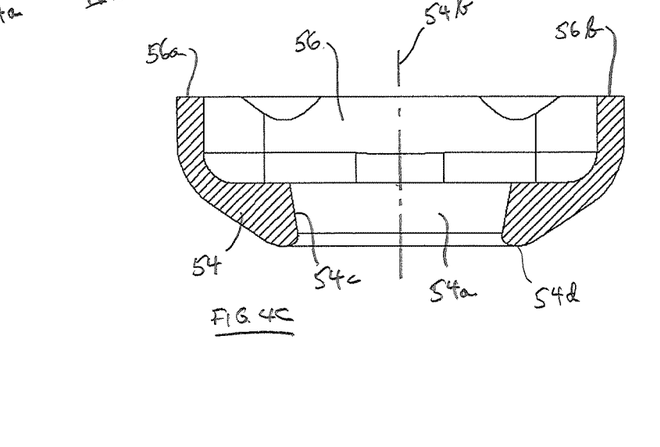

Referring now to FIGS. 4A, 4B and 4C and FIGS. 5A, 5B, 5C and 5D, further details of the base 26 of coupling assembly 22 are described. Lower base 26a is depicted in FIGS. 4A, 4B and 4C. Lower base 26a includes a bottom wall 54 having an opening 54a extending therethrough and defining a base opening axis 54b. A peripheral wall 56 projects upwardly from bottom wall 54 and extends around the periphery of bottom wall 54. Peripheral 56 in a particular arrangement extends continuously around bottom wall 54 defining with bottom wall 54 a basin 58. Opening 54a communicates with basin 58 and is configured to support head 32 of bone screw 16 for polyaxial movement of bone engaging shank 18 relative thereto. In a particular aspect, opening 54a is configured to have an interior conical surface 54c having a diameter adjacent a bottom surface 54d of bottom wall that is smaller than the maximum diameter of head 32 of bone screw 16. In a further particular aspect, lower base 26a has a generally rectangular configuration wherein peripheral wall 56 is defined by spaced opposing end walls 56a and 56b and spaced opposing side walls 56c and 56d extending therebetween. In this aspect, opening 54a extending through bottom wall 54 is eccentrically disposed therethrough such that base opening axis 54b is closer to side wall 56d than to side wall 56c, as shown in FIG. 4B.

Figure 5A:
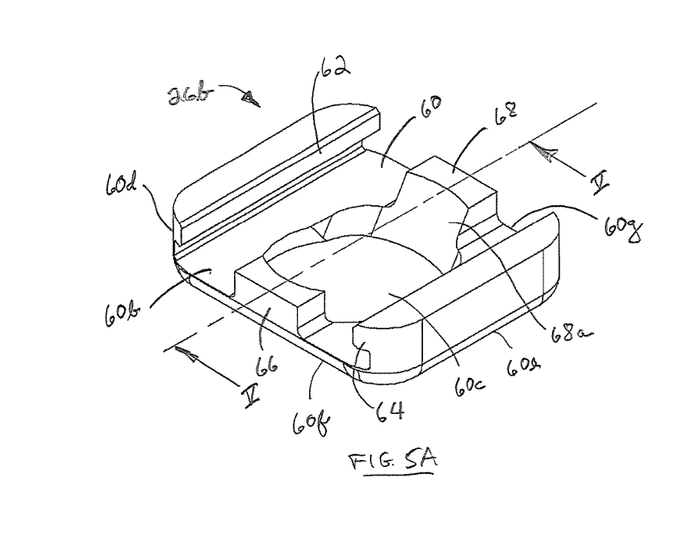
FIG. 5A is a top perspective view of the upper base of the bone screw assembly of FIG. 1.
Figure 5B:
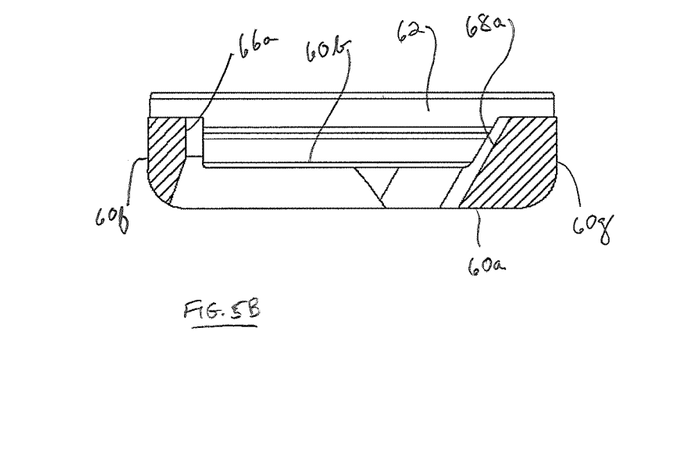
FIG. 5B is a cross-sectional view of the upper base as seen along viewing lines V-V of FIG. 5A.
Figure 5C:
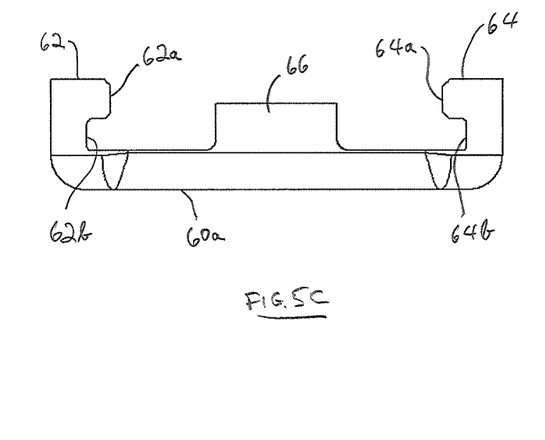
FIG. 5C is a side elevation view of the upper base of FIG. 5A.
Figure 5D:
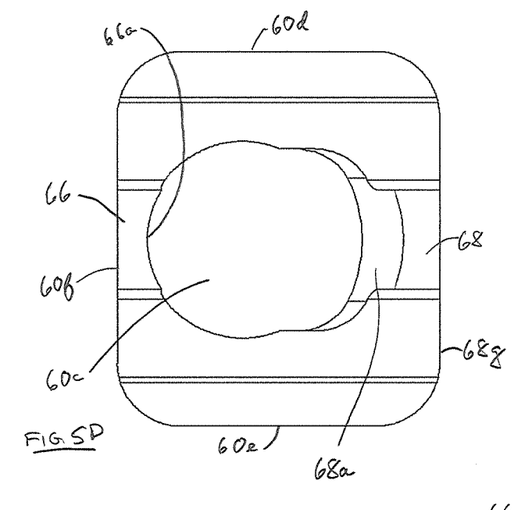
FIG. 5D is a top plan view of the upper base of FIG. 5A.

Turning now to FIGS. 5A, 5B, 5C and 5D, details of upper base 26b are described. Upper base 26b includes a substantially flat plate 60 have a bottom surface 60a and a top surface 60b. Bottom surface 60a is configured to be supported by bottom wall 54 of lower base 26a, as will be described. Upper base 26b has an opening 60c extending through bottom surface 60a and top surface 60b of plate 60. In a particular aspect, upper base 26b has a generally rectangular configuration to be closely received within basin 58 of lower base 26a. In this arrangement, upper base 26b has spaced opposing end edges 60d and 60e and spaced opposing side edges 60f and 60g extending therebetween. Opening 60c through plate 60 is eccentrically disposed, as illustrated in FIG. 5D and the maximum dimension of opening 60c is greater than the maximum diameter of opening 54a of lower base 26a.

Upper base 26b is formed to include a pair of spaced substantially parallel rails 62 and 64 extending across top surface 60b of plate 60 that defines structure for cooperative sliding coupling with yoke 20, as will be described. Each rail 62 and 64 is disposed on opposite sides of the opening 60c, with rail 62 being located adjacent end edge 60d and rail 64 being located adjacent end edge 60e. In one aspect, each rail 62 and 64 includes an inwardly projecting flange 62a and 64a, respectively, and an outwardly directed groove 62b and 64b, respectively, as shown in FIG. 5C. As such, rails 62 and 64 together form a T-slot configuration for slidable cooperative fit with the T-bar configuration of base yoke 20, as described hereinabove. Formed additionally on upper base 26b are a pair of opposing upstanding walls 66 and 68 projecting upwardly from plate 60. Upstanding wall 66 is located adjacent side edge 60f of plate 60 and upstanding wall 68 is located adjacent side edge 60g. Upstanding wall 66 has a curved surface 66a communicating with opening 60c as shown in FIG. 5D. Upstanding wall 68 has a curved tapered surface 68a communicating with opening 60c, the purpose of which will be described hereinbelow. Curved tapered surface 68a is disposed substantially opposite curved surface 66a and tapers upwardly and outwardly from bottom surface 60a of plate 60 toward top surface 60b as shown in FIG. 5B.

Figure 6A:
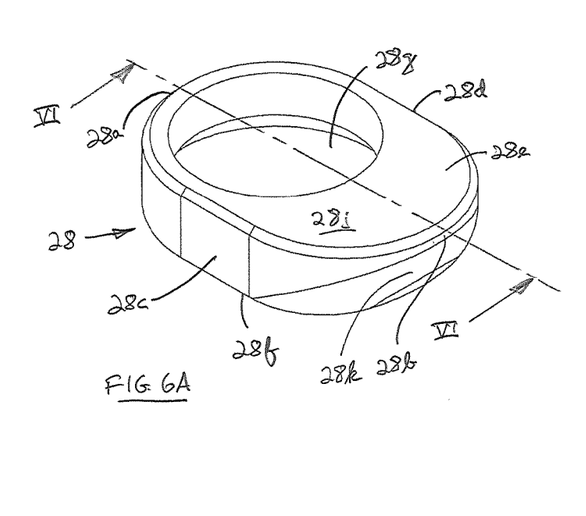
FIG. 6A is a top perspective view of the pressure element of the bone screw assembly of FIG. 1.
Figure 6B:
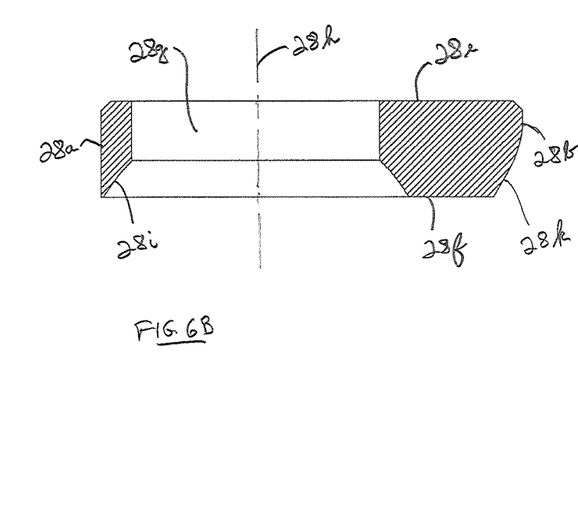
FIG. 6B is a cross-sectional view of the pressure element as seen along viewing lines VI-VI of FIG. 6A.
Figure 6C:
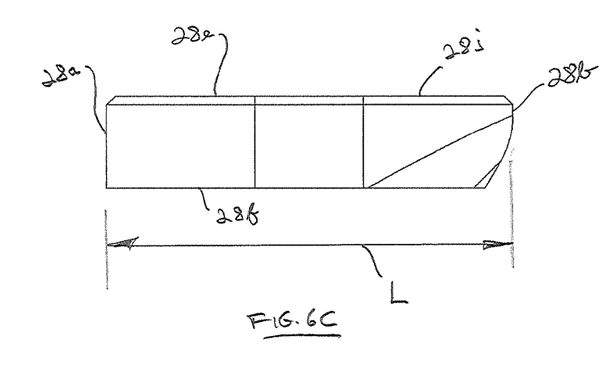
FIG. 6C is a side elevation view of the pressure element of FIG. 6A.
Figure 6D:
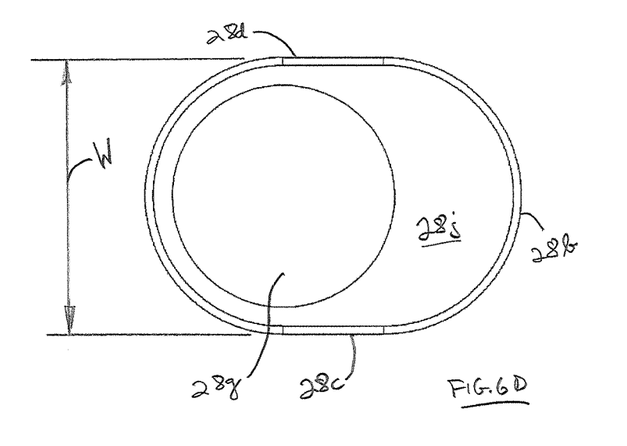
FIG. 6D is a top plan view of the pressure element of FIG. 6A.

Referring now to FIGS. 6A, 6B, 6C and 6D, details of pressure element 28 are described. Pressure element 28 comprises a first end 28a and a spaced substantially opposite end 28b with a pair of spaced sidewalls 28c and 28d extending therebetween. Pressure element is configured to be received within opening 60c of upper base 26b with pressure elements ends 28a and 28b being curved to have a substantially similar radius of curvature as curved surfaces 66a and 68a of upper base 26b, respectively. Pressure element 28 includes an upper surface 28e and a lower surface 28f and an opening 28g extending through upper surface 28e and lower surface 28f defining a pressure element opening axis 28h. Opening 28g has a substantially spherical surface portion 28i communicating with lower surface 28f for engagement with the substantially spherical outer surface 32a of bone screw head 32. In one aspect, pressure element 28 is oblong having a length, L greater than a width, W as shown in FIGS. 6C and 6D. In this arrangement, opening 28g through pressure element 28 is eccentrically disposed such that pressure element opening axis 28h is closer to first end 28a than opposite end 28b as depicted in FIG. 6B. The eccentric location of opening 28g defines an extended surface area 28j on upper surface 28e of pressure element 28 between pressure element opening 28g and opposite end 28b of pressure element 28, as shown particularly in FIGS. 6A and 6D. Opposite end 28b is further formed to include a tapered surface 28k for cooperative engagement with tapered surface 68a of upper base 28b, as will be described.

Figure 7A:
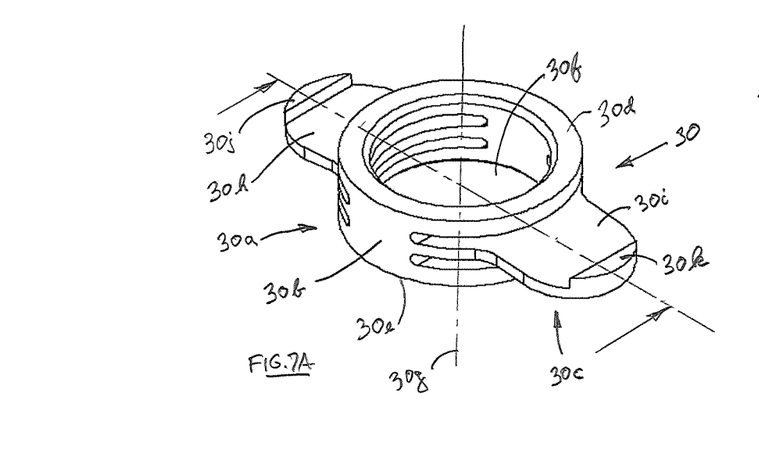
FIG. 7A is a top perspective view of the spring element of the bone screw assembly of FIG. 1.
Figure 7B:
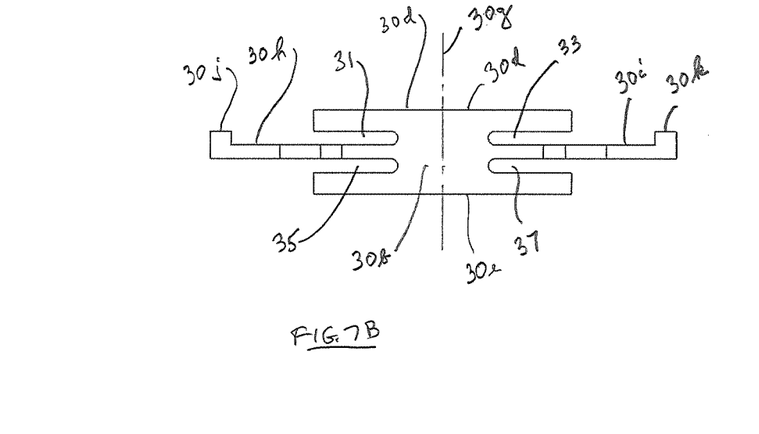
FIG. 7B is a side elevation view of the spring element of FIG. 7A.
Figure 7C:
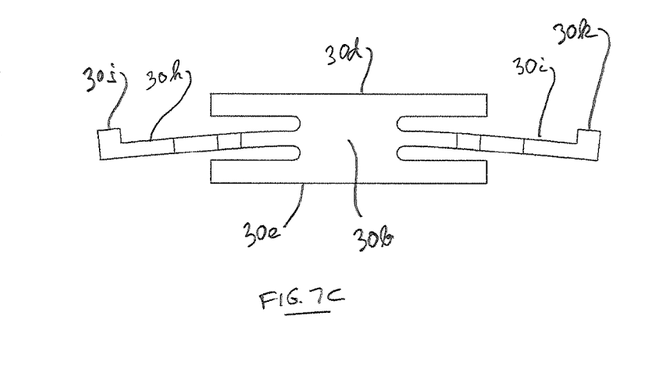
FIG. 7C is a side elevation view showing the cantilevered arms of the spring element of FIG. 7A in a flexed position.
Figure 7D:
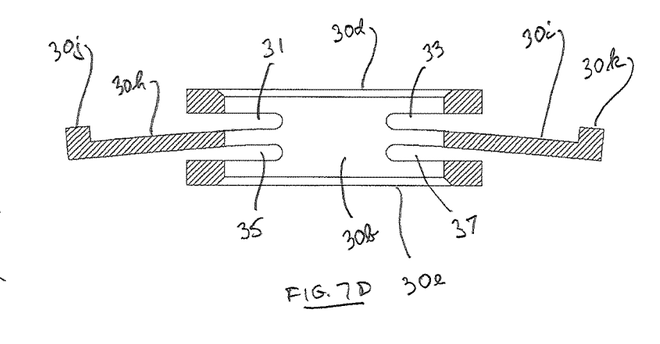
FIG. 7D is a cross-sectional view of the spring element shown in the condition of FIG. 7C.

Turning now to FIGS. 7A, 7B, 7C and 7D, details of spring element 30 are described. Spring element 30 comprises a plate 30a including a generally cylindrical central hub 30b and a resiliently flexible member 30c projecting outwardly therefrom. In a particular arrangement, hub 30b is solid and substantially incompressible and includes a top surface 30d and a bottom surface 30e. An opening 30f extends through top surface 30d and bottom surface 30e defining a spring opening axis 30g. In a further particular arrangement, resiliently flexible member 30c comprises a pair of cantilevered arms 30h and 30i projecting outwardly radially from hub 30b in substantially opposite directions. Each of arms 30h and 30i includes at a location distal from hub 30b a projecting lip 30j and 30k, respectively. Each of said lips 30j and 30k define an elevated contact surface for engagement with contact surface 20c at opposite end 20b of yoke 20, as will be described. Hub 30b has an upper groove 31 and 33 respectively extending into hub 30b above each of arms 30h and 30i, and a lower groove 35 and 37 extending into hub 30b below each of arms 30h and 30i. Grooves 31,33 and 35, 37 facilitate suitable bending of arms 30h and 30i as illustrated in FIGS. 7C and 7D. While a pair of cantilevered arms 30h and 30i is described, it should be appreciated that flexible member 30c of spring element 30 may comprise a single member or more than two arms. In one aspect, spring element 30 is formed of titanium or other suitable biocompatible spring material.

Figure 8A:
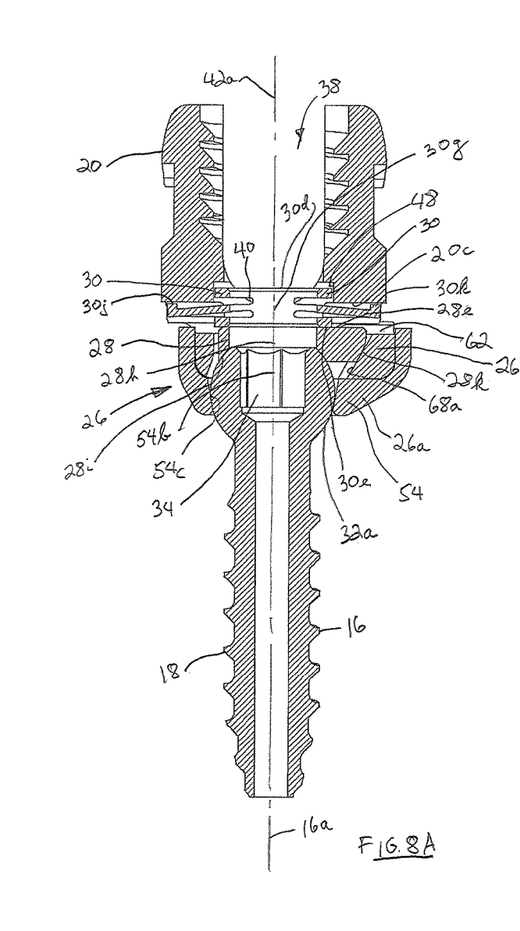

Having described the details of the components of the translating polyaxial bone screw assembly 14, the assembly of the components to form the assembled screw assembly 14 as shown in FIGS. 8A and 8B. Base 26 is formed by placing upper base 26b into basin 58 of lower base 26a until bottom surface 60a upper base 26b is supported on bottom wall 54 of lower base 26a. Opening 60c of upper base 26b is in communication with opening 54a of lower base 26a. Lower base 26a and upper base 26b are fixedly attached such as by spot welding or other suitable joining techniques. Elongate threaded shaft 18 of bone screw 16 is introduced through opening 54a of lower base 26a until head 32 of bone screw 16 engages conical surface 54c, thereby supporting bone screw 16 for polyaxial movement relative to base 26. Pressure element 28 is inserted into opening 60c of upper base 26b with tapered end 28b being placed in contact with curved tapered surface 68a of upper base 26b and spherical surface portion 28i of opening 28g in engagement with the substantially spherical outer surface 32a of bone screw head 32. Opening 28g of pressure element 28 is in communication with opening 60c of upper base 26b.

Hub top surface 30d of spring element 30 is placed into counterbore 48 at opposite end 20b of yoke 20 and yoke rails 50, 52 are cooperatively slidingly engaged with base rails 62, 64. In the process of coupling yoke 20 with base 26, flexible cantilevered arms 30h and 30i are caused to flex with lips 30j and 30k contacting yoke contact surface 20c with a bias force. Bottom surface 30e of spring element 30 engages upper surface 28e of pressure element 28 and applies pressure thereto under the bias force produced by spring arms 30h and 30i. The pressure applied to pressure element 28 causes tapered surface 28k of pressure element 28 to wedge distally against curved tapered surface 68a of upper base 26b, thereby biasing spherical surface portion 28i of opening 28g against substantially spherical outer surface 32a of bone screw head 32. At this point, bone screw assembly 14 is assembled and ready for receipt of rod 12 with spring element 30 serving as a biasing element applying a tension force between yoke 20 and bone screw 16 sufficient to hold yoke 20 and bone screw 16 in a provisional position that is surmountable upon application of a manual force.

As assembled, hub 30b is situated within counterbore 48 such that top surface 30d is spaced proximally above bottom surface 40 of yoke channel 38 and intersects channel 38 with counterbore 48 constraining spring element 30 for joint movement with yoke 20. As so arranged, upon introduction of rod 12 into yoke 38 as will be described, rod 12 will engage hub top surface 30d to apply locking pressure through hub 30b to pressure element 28 and to head 32 of bone screw 16, as will be described. In a first position of screw assembly 14, which is illustrated in FIGS. 8A and 8B, yoke opening axis 42a, spring element opening axis 30g, pressure element opening axis 28h, base opening axis 54b and said screw axis 16a are all substantially collinear. In this position, bone screw assembly 14 is ready for use as follows.

Figure 9A:
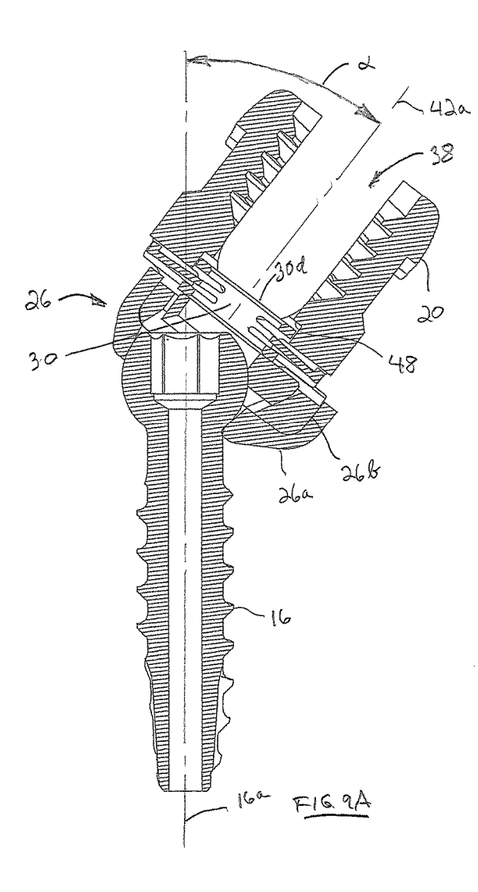
FIG. 9A is the cross-sectional view of FIG. 8A showing the yoke in an angulated position relative to the bone screw.
Figure 9B:
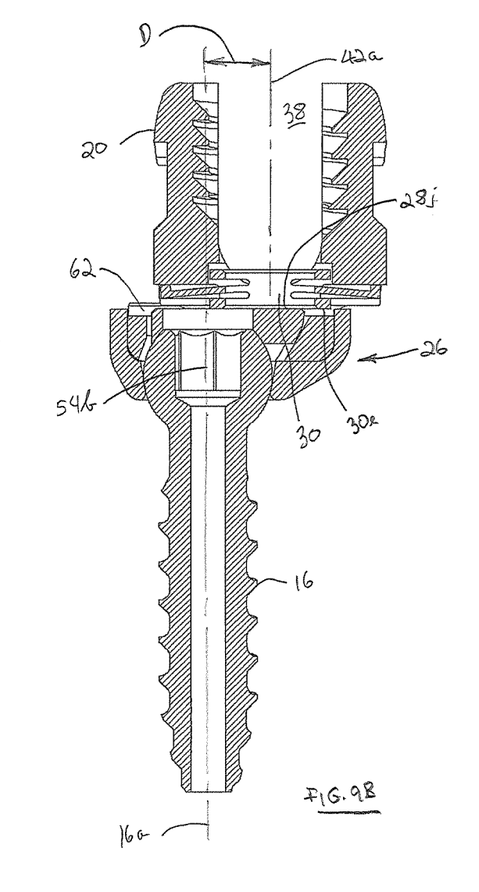
FIG. 9B is the cross-sectional view of FIG. 8A showing the yoke in a translated position relative to the bone screw.

With all the openings of the components of bone screw assembly 14 being substantially aligned as shown in FIGS. 8A and 8B, a suitable driving instrument may be engaged with socket 34 of bone screw 16 in a manner to threadably attach bone screw assembly 14 to a vertebra in the spine. Upon proper insertion of threaded shank 18 into the desired vertebra, yoke 20 is maintained in a provisional holding position which may be manipulated by a surgeon translationally and polyaxially depending upon the spinal anatomy of the patient prior to receiving the connecting rod 12. As a result of the slidable coupling of yoke 20 with upper base 26b and the fixed attachment of upper base 26b to lower base 26a, yoke channel 38 can swivel in articulating movement jointly with base 26 at an angle, a about screw axis 16a, as shown in FIG. 9A upon application of a suitable manual force to surmount the tension force applied by spring element 30. With top surface 30d of spring hub 30b being captured within counterbore 48 of yoke 20, spring element 30 will likewise articulate jointly with yoke 20 while maintaining tension between yoke 20 and bone screw 16 in a manipulable provisional position. Additionally, yoke 20 can translate linearly relative to base 26 upon application of a suitable manual force in the direction of translation axis 53 to surmount the tension force applied by spring element 30. Yoke 20 will slide linearly on base 26 as a result of the cooperative sliding coupling between yoke rails 50, 52 and base rails 62, 64, as shown in FIG. 9B. Upon such movement, yoke channel 38 will be translated from first position as shown in FIG. 8A wherein yoke opening axis 42a is substantially coincident with bone screw axis 16a to a second position wherein yoke channel 38 and yoke axis 42a are offset laterally by a distance, D as shown in FIG. 9B relative to base opening axis 54b and bone screw axis 16a. During translational movement of yoke 20, bottom surface 30e of spring element 30, the hub of which is captured in counterbore 48 of yoke 20, slides on extended surface area 28j of pressure element 28 toward said opposite end 28b, allowing the tension force between yoke 20 and bone screw 16 to be applied during such relative movement. Accordingly, the manipulable provisional position is maintained during translation of yoke relative to base 26. It should be understood that polyaxial and translational movement of yoke 20 relative to bone screw 16 may be provided together or separately. It should also be understood that the particular bone screw assembly 14 shown and described allows for translation of yoke 20 in only one direction laterally from the first position wherein the yoke opening axis 42a is aligned with the bone screw axis 16a, the purpose of which is described below.

Upon the desired polyaxial or translational movement of yoke channel 38 relative to bone screw 16, a connecting rod 12 may be introduced into yoke channel 38 of one or more bone screw assemblies 14. Turning now to FIGS. 10A and 10B, the assembly of the connecting rod 12 to translating polyaxial bone screw 14 to form spinal fixation system 10 is shown. Rod 12 is initially placed between the arms 36a and 36b of yoke 20 to rest on top surface 30d of spring element 30. Yoke channel 38 may then be closed with fastening element 24 to secure the rod 12 within. Before rod 12 is secured, it should be appreciated that rod 12 may be adjusted longitudinally within channel 38 and yoke 20 with rod 12 therein may swivel polyaxially (as shown in FIG. 9A) or translate laterally (as shown in FIG. 10B) relative to bone screw 16. The combination of polyaxial and translating movement of yoke 20 relative to bone screw 16 allows for proper rod placement in the spine with minimal rod bending.

After the surgeon makes spinal adjustments of rod 12 in the spinal construct, fastening element 24, preferably in the form of a set screw with external threads, is threadably engaged with internal threads 44 of yoke arms 36a and 36b. As set screw 24 is tightened, it presses rod 12 against top surface 30d of hub 30b of spring element 30. As set screw 24 is further driven into internal threads 44 of yoke 20, set screw 24 pushes rod 12 downwardly against hub 30b which in turn applies additional force against pressure element 28 causing pressure element 28 to wedge tightly against bone screw head 32 while pulling base 26 upwardly, thereby overcoming the provisional tension force, securing elongate connecting rod 12 within yoke channel 38 and locking yoke 20 relative to bone screw 16 in a secure bone screw assembly 14

Figure 11A:
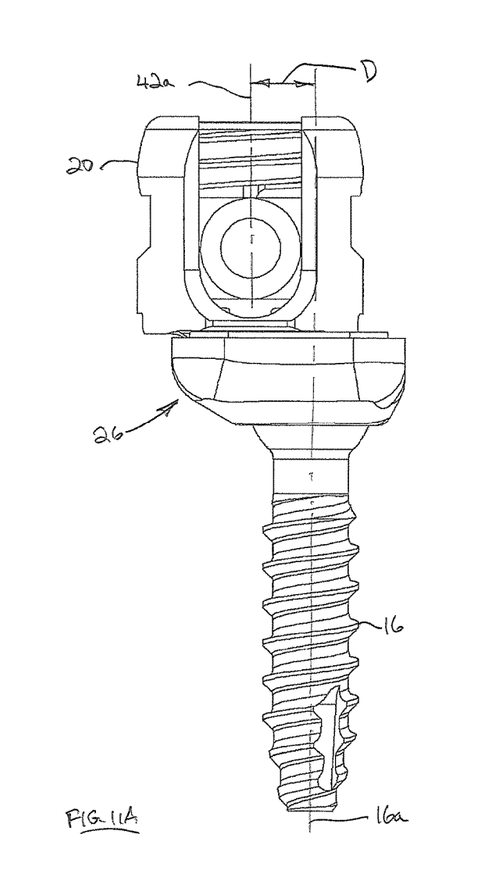
FIG. 11A is a side elevation view of the bone screw assembly with the yoke in the translated position of FIG. 10B.
Figure 11B:
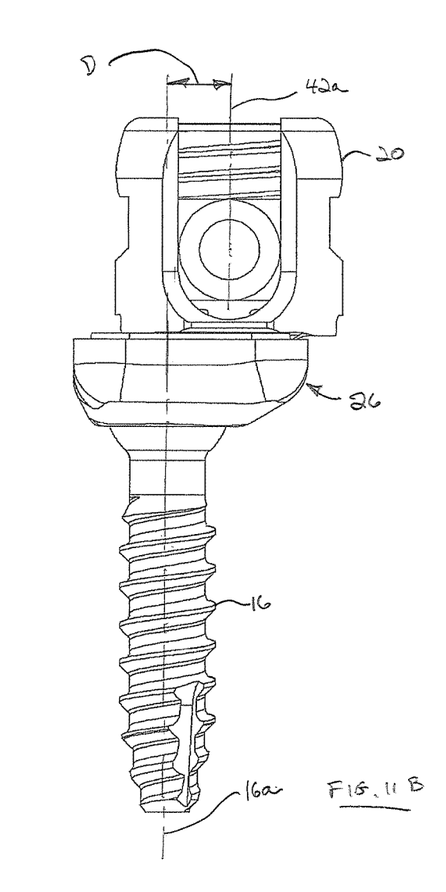
FIG. 11B is a side elevation view of the bone screw assembly with the yoke in the translated position of FIG. 10B and with the yoke having been rotated 180° about bone screw axis.

It should now be appreciated that translating polyaxial bone screw assembly 14 allows for suitable placement of bone screw 16 without compromising rod alignment. Such alignment allows screw assembly 14 to be placed with optimal purchase in the pedicle of a vertebra without the need to over bend rod 12 and to more easily align yoke channels 38 of adjacent screw assemblies 14. In a particular arrangement, translating polyaxial bone screw assembly 14 has particular application in cervico thoracic surgery, in both open and mini open techniques. The bone screw assembly 14 allows for difficult pedicle or lateral mass screw placement and easier transitions from C1-C3 and C6-T3 while allowing the profile of yokes 20 to be kept relatively small for less impedance with surrounding tissue. Screw diameters of 3.8 mm, 4.2 mm, 4.6 mm, 5.0 mm and 5.5 mm and the respective screw lengths are suited for both lateral mass and pedicle screw placement. 3.5 mm and 4.0 mm connecting rod sizes are the most common cervico thoracic rods in use. With such rod sizes, the subject bone screw assembly 14 may realize an articulation angle, a of up to about 40°. Also with such rod sizes, yoke channel 38 may be laterally offset from the axis 16a of bone screw 16 by a distance, D of up to about 2.5 mm, as shown in FIG. 11A. With yoke 20 being rotatable about bone screw axis 16a, the lateral offset may be adjusted from a position directed outwardly from the spinal midline to a position directed inwardly of the midline simply by rotating base 26 about bone screw 16, thereby providing greater flexibility to the surgeon during a spinal procedure. As such, the lateral offset may range up to about 5.0 mm in this particular embodiment. It should be appreciated, however, that the angulation and offset dimensions are exemplary and that other angles, a and offset distances, D may be realized in accordance with the inventive concepts described herein.

While the invention has been illustrated and described in detail in the drawings and foregoing description, it should be understood that such description is illustrative and not limiting. For example, the tension force described herein as provided by spring element 30 may be combined with a grit blasting of the outer surface 32a of the head 32 of bone screw 16 to amplify stiction felt by an operator. During use, this produces a frictional feel which aids in tactile feedback while manipulating yoke 20. Further, cannulated and non-cannulated versions of bone screws 16 may be provided to assist with mini open techniques. Additionally, standard and extended tab screw versions may be provided to help with mini open techniques and rod connecting rod reduction. It should therefore be understood that various changes, modifications and further applications may be made without departing from the spirit of the invention and the scope of the appended claims.

What is claimed is:

1. A translating polyaxial bone screw assembly for anchoring an elongate connecting rod to a vertebra of a spine, comprising:
    a bone screw having a threaded bone engaging shank defining a screw axis and a head, said head including an outer surface;
    a yoke having at one end a rod receiving channel defining a channel axis for receiving an elongate connecting rod and an opposite end;
    a coupling assembly coupling said opposite end of said yoke to the head of said bone screw for joint polyaxial movement of said yoke about the axis of said bone screw and translational movement of said yoke channel in a direction transverse to the axis of said bone screw, said coupling assembly comprising a biasing element supported between said yoke and the head of said bone screw for joint movement with said yoke and providing a manually surmountable tension force between said yoke and the head of said bone screw that is maintained during polyaxial and translational movement of said yoke relative to said bone screw, said biasing element comprising a spring element including a central hub and a resiliently flexible member comprising a pair of cantilevered arms projecting outwardly from said hub, each of cantilevered arms engaging a contact surface on the opposite end of said yoke; and
    a fastening element supported by said yoke for securing said elongate connecting rod within said channel and for locking said yoke relative to said bone screw.

2. The bone screw assembly of claim 1, wherein said yoke includes a pair of arms defining said yoke channel therebetween and spaced by a bottom surface, and wherein said yoke has an opening defining a yoke opening axis extending through said bottom surface in communication with said channel.

3. The bone screw assembly of claim 2, wherein said hub is generally cylindrical having a top surface and a bottom surface and wherein said arms project outwardly radially from said hub in substantially opposite directions.

4. The bone screw assembly of claim 3, wherein said hub has an upper groove extending into said hub above each of said arms and a lower groove extending into said hub below each of said arms.

5. The bone screw assembly of claim 4, wherein said opening through said bottom surface of said yoke includes a counterbore extending into said yoke at the opposite end thereof, and wherein said hub is situated within said counterbore such that said top surface is spaced from said bottom surface of said channel and intersects said channel, said counterbore constraining said spring element for joint movement with said yoke.

6. The bone screw assembly of claim 5, wherein each of said arms includes a lip adjacent a distal end of each arm, each of said lips defining an elevated contact surface in engagement with the contact surface at the opposite end of said yoke.

7. The bone screw assembly of claim 1, wherein said coupling assembly comprises a base including a bottom wall having an opening therethrough defining a base opening axis, said bottom wall supporting the head of said bone screw for polyaxial movement of said bone engaging shank relative thereto, said opposite end of said yoke and said base having cooperative coupling structure that provides sliding movement of said yoke channel relative to said base.

8. The bone screw assembly of claim 7, wherein said cooperative coupling structure includes a pair of spaced rails extending across the opposite end of said yoke in a direction transverse to said channel axis, one rail being disposed on each side of the opening of said yoke, and wherein said cooperative structure includes a pair of spaced rails extending across said base, one rail being disposed on each side of said base opening, the rails at the opposite end of said yoke being in sliding engagement with the rails of said base.

9. The bone screw assembly of claim 8, wherein said base comprises opposing ends and spaced opposing sides extending therebetween, each of said base rails being located respectively adjacent said opposing sides, said opening through said bottom wall of said base being eccentrically disposed therethrough such that said base opening axis is closer to one of said sides than said spaced opposing side.

10. The bone screw assembly of claim 9, wherein said base is configured to allow linear translation of said yoke channel from a first position relative to said base opening axis to a second position wherein said yoke channel is offset laterally relative to said base opening axis.

11. The bone screw assembly of claim 10, wherein said yoke channel in said first position is substantially coincident with said base opening axis.

12. The bone screw assembly of claim 3, wherein said coupling assembly comprises a pressure element supported by said base, said pressure element including an upper surface engaging said lower surface of said spring element hub and a lower surface engaging the head of said bone screw.

13. A translating polyaxial bone screw assembly for anchoring an elongate connecting rod to a vertebra of a spine, comprising:

a bone screw having a threaded bone engaging shank defining a screw axis and a head, said head including an outer surface;

a yoke having at one end a rod receiving channel defining a channel axis for receiving an elongate connecting rod and an opposite end;

a base supporting the head of said bone screw in a manner allowing polyaxial movement of said bone engaging shank relative to said base, said base being coupled to said opposite end of said yoke for sliding translational movement of said yoke channel relative to said base in a direction transverse to the axis of said bone screw;

a pressure element supported by said base, said pressure element including an upper surface and a lower surface, a portion of said pressure element engaging the head of said bone screw;

a spring element supported between said opposite end of said yoke and said pressure element and being movable jointly with said yoke, said spring element comprising a top surface, a bottom surface and a resiliently flexible portion projecting therefrom, said bottom surface engaging the upper surface of said pressure element and said resilient flexible portion engaging the opposite end of said yoke under a spring biased applying a tension force between said yoke and said bone screw sufficient to hold said yoke and said bone screw in a provisional position that is surmountable upon application of a manual force; and a fastening element supported by said yoke for securing said elongate connecting rod within said channel and for locking said yoke relative to said bone screw.

14. The bone screw assembly of claim 13, wherein said yoke includes a pair of arms defining said yoke channel therebetween and spaced by a bottom surface, and wherein said yoke has an opening defining a yoke opening axis extending through said bottom surface of said yoke channel in communication with said channel.

15. The bone screw assembly of claim 14, wherein said spring element has an opening extending through said top surface and said bottom surface defining a spring opening axis.

16. The bone screw assembly of claim 15, wherein said base includes a bottom wall having an opening therethrough defining a base opening axis, said bottom wall supporting the head of said bone screw for polyaxial movement of said bone engaging shank relative thereto, said opposite end of said yoke and said base having cooperative coupling structure that provides sliding movement of said yoke relative to said base.

17. The bone screw assembly of claim 16, wherein said pressure element has an opening extending through said upper surface and said lower surface defining a pressure element opening axis.

18. The bone screw assembly of claim 17, wherein said bone screw has a socket extending into the head of said bone screw along said screw axis.

19. The bone screw assembly of claim 18, wherein in a first position, said yoke opening axis, said spring element opening axis, said pressure element opening axis, said base opening axis and said screw axis are substantially collinear.

20. The bone screw assembly of claim 19, wherein said pressure element is oblong having a length greater than a width, and wherein said opening through said pressure element is eccentrically disposed such that said pressure element opening axis is closer to one end of said pressure element defining thereby an extended surface area on the upper surface of said pressure element between said pressure element opening and an opposite end of said pressure element.

21. The bone screw assembly of claim 20, wherein upon sliding movement of said yoke relative to said base, the bottom surface of said spring element slides on said extended surface of said pressure element toward said opposite end thereof, whereby said yoke opening axis and said spring element opening axis are offset from said pressure element opening axis while the tension force between said yoke and said bone screw is maintained during such relative movement of said yoke and spring element.

22. A translating polyaxial bone screw assembly for anchoring an elongate connecting rod to a vertebra of a spine, comprising:

a bone screw having a threaded bone engaging shank defining a screw axis and a head, said head including an outer surface;

a yoke having at one end a rod receiving channel defining a channel axis for receiving an elongate connecting rod and an opposite end, said yoke including a pair of arms defining said yoke channel therebetween and spaced by a bottom surface, and wherein said yoke has an opening extending through said bottom surface in communication with said channel;

a lower base including a bottom wall having an opening therethrough defining a base opening axis, said bottom wall supporting the head of said bone screw for polyaxial movement of said bone engaging shank relative thereto;

an upper base fixedly supported by said lower base, said upper base including a bottom surface supported by the bottom wall of said lower base, said upper base having an opening extending therethrough in communication with the opening through said lower base, said opposite end of said yoke and said upper base having cooperative coupling structure that provides sliding movement of said yoke channel relative to said upper base and thereby said lower base in a direction transverse to the base opening axis;

a pressure element supported by said upper base, said pressure element including an upper surface and a lower surface and an opening extending through said upper surface and said lower surface in communication with the opening through said upper base, a portion of said pressure element engaging the head of said bone screw;

a spring element supported between said opposite end of said yoke and said pressure element and being movable jointly with said yoke, said spring element comprising a top surface, a bottom surface and a resiliently flexible portion projecting therefrom, said spring element having an opening extending through said top surface and bottom surface in communication with the opening through said pressure element and the opening through said yoke, said bottom surface of said spring element engaging the upper surface of said pressure element and said resilient flexible portion of said spring element engaging the opposite end of said yoke under a spring bias applying a tension force between said yoke and said pressure element and thereby to the head of said bone screw sufficient to hold said yoke and said bone screw in a provisional position that is surmountable upon application of a manual force; and a fastening element supported by said yoke for securing said elongate connecting rod within said channel and for locking said yoke relative to said bone screw.

23. The bone screw assembly of claim 22, wherein said spring element comprises a spring plate including a generally cylindrical central hub that is solid and substantially incompressible, said hub having a top surface and a bottom surface, wherein said resiliently flexible member comprises a pair of cantilevered arms projecting outwardly radially from said hub in substantially opposite directions, each of said arms contacting said opposite end of said yoke, said bottom surface of said hub contacting said upper surface of said pressure element and said top surface of said hub being received within said opening of said yoke in a manner to constrain said spring plate for joint movement with said yoke.

24. The bone screw assembly of claim 23, wherein said cooperative coupling structure includes a pair of spaced rails extending across the opposite end of said yoke in a direction transverse to said channel axis, one rail being disposed on each side of the opening of said yoke, and wherein said cooperative structure includes a pair of spaced rails extending across said base, one rail being disposed on each side of said base opening, the rails at the opposite end of said yoke being in sliding engagement with the rails of said base.

25. The bone screw assembly of claim 24, wherein said pressure element and said upper base include cooperative tapered surfaces in engagement with each other that upon application of said tension force by said spring plate causes said pressure element to be urged toward the head of said bone screw.

26. The bone screw assembly of claim 25, wherein the outer surface of the head of said bone screw is substantially spherical, and wherein the opening extending through said pressure element has a substantially spherical surface portion in engagement with the substantially spherical outer surface of the head of said bone screw.

* * * * *

UNITED STATES PATENT AND TRADEMARK OFFICE
CERTIFICATE OF CORRECTION

Page 1 of 1

PATENT NO. : 10,070,897 B1
APPLICATION NO. : 15/846959
DATED : September 11, 2018
INVENTOR(S) : Zachary Gregory et al.

It is certified that error appears in the above-identified patent and that said Letters Patent is hereby corrected as shown below:

In the Specification

Column 3, Line 10, "is the cross-sectional views of". Should read instead as --is the cross-sectional view of--.

Column 3, Line 14, "is the cross-sectional views of". Should read instead as --is the cross-sectional view of--.

In the Claims

Column 11, Claim 13, Line 25, "spring biased applying a". Should read instead as --spring bias applying a--.

Signed and Sealed this
Fifth Day of February, 2019

Andrei Iancu
*Director of the United States Patent and Trademark Office*